United States Patent
Chen

(10) Patent No.: US 10,526,118 B2
(45) Date of Patent: Jan. 7, 2020

(54) POSITION INDICATOR ON LIQUID SAMPLE CONTAINER

(75) Inventor: Jianfeng Chen, San Ramon, CA (US)

(73) Assignee: Amedica Biotech, Inc., Hayward, CA (US)

( * ) Notice: Subject to any disclaimer, the term of this patent is extended or adjusted under 35 U.S.C. 154(b) by 0 days.

(21) Appl. No.: 13/590,180

(22) Filed: Aug. 20, 2012

(65) Prior Publication Data

US 2013/0068649 A1 Mar. 21, 2013

Related U.S. Application Data

(60) Provisional application No. 61/525,062, filed on Aug. 18, 2011.

(51) Int. Cl.
*B65D 55/02* (2006.01)
*B01L 3/00* (2006.01)
*G01N 33/493* (2006.01)

(52) U.S. Cl.
CPC ........ *B65D 55/024* (2013.01); *B01L 3/50825* (2013.01); *B65D 55/02* (2013.01); *G01N 33/493* (2013.01); *B01L 2200/141* (2013.01); *B01L 2200/145* (2013.01); *B01L 2300/046* (2013.01); *B65D 2203/00* (2013.01)

(58) Field of Classification Search
CPC ........ B65D 39/00; B65D 51/24; B65D 41/04; B65D 55/024
USPC ....... 215/230, 329; 206/459.1; 220/330, 331
See application file for complete search history.

(56) References Cited

U.S. PATENT DOCUMENTS

| 4,461,394 A | * | 7/1984 | Sendel | B65D 41/0471 215/330 |
|---|---|---|---|---|
| 5,803,287 A | * | 9/1998 | Kusz | B65D 41/0471 215/330 |
| 6,003,467 A | * | 12/1999 | Shelton-Ferrell | G09F 11/23 116/308 |
| 6,230,924 B1 | * | 5/2001 | Weiss | B29C 51/32 220/366.1 |
| 6,277,646 B1 | | 8/2001 | Guirguis et al. | |
| 6,871,752 B2 | * | 3/2005 | Montgomery | B65D 41/0414 215/219 |
| 2005/0106750 A1 | | 5/2005 | Tung et al. | |
| 2005/0133396 A1 | * | 6/2005 | Daykin | 206/459.1 |

(Continued)

FOREIGN PATENT DOCUMENTS

WO WO2011060623 A1 5/2011

*Primary Examiner* — Anthony D Stashick
*Assistant Examiner* — Raven Collins
(74) *Attorney, Agent, or Firm* — DLA Piper LLP (US)

(57) ABSTRACT

A disclosed technique includes an assembly comprising a cup with a first visual sealing indicator and a lid with a second visual sealing indicator wherein, in operation, the lid is screwed on the cup to a sealing indicator position where the first visual sealing indicator and the second visual sealing indicator are aligned. Another disclosed technique includes an assembly comprising a cup with a first audible sealing indicator and a lid with a second audible sealing indicator wherein, in operation, the lid is screwed on the cup to a position past where the first audible sealing indicator and the second audible sealing indicator have contacted each other producing an audible sound. Another disclosed technique includes a cup with a raised central bottom area and an insert with bracing wings wherein, in operation, the bracing wings stabilize and secure the insert in the cup.

12 Claims, 6 Drawing Sheets

(56) References Cited

U.S. PATENT DOCUMENTS

2008/0099423 A1\* 5/2008 Koch ........................... 215/230
2008/0257851 A1\* 10/2008 Vargas ......................... 215/230

\* cited by examiner

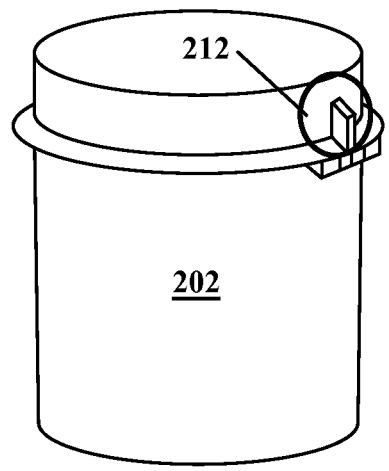
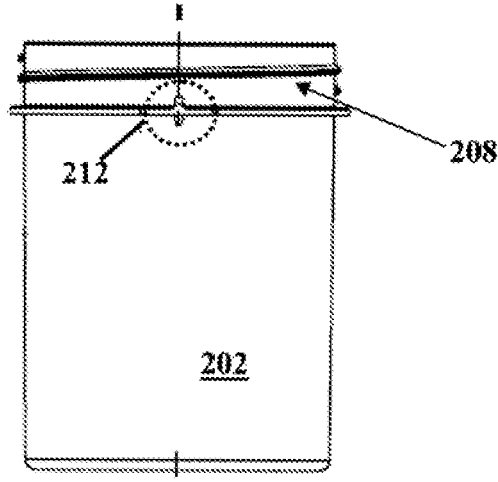
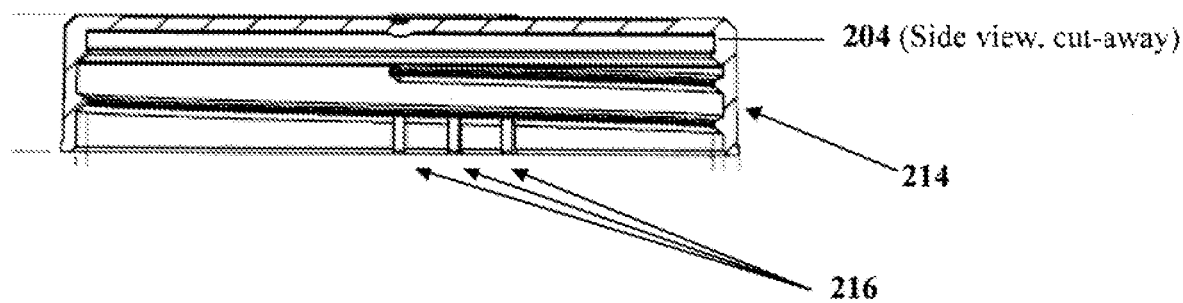
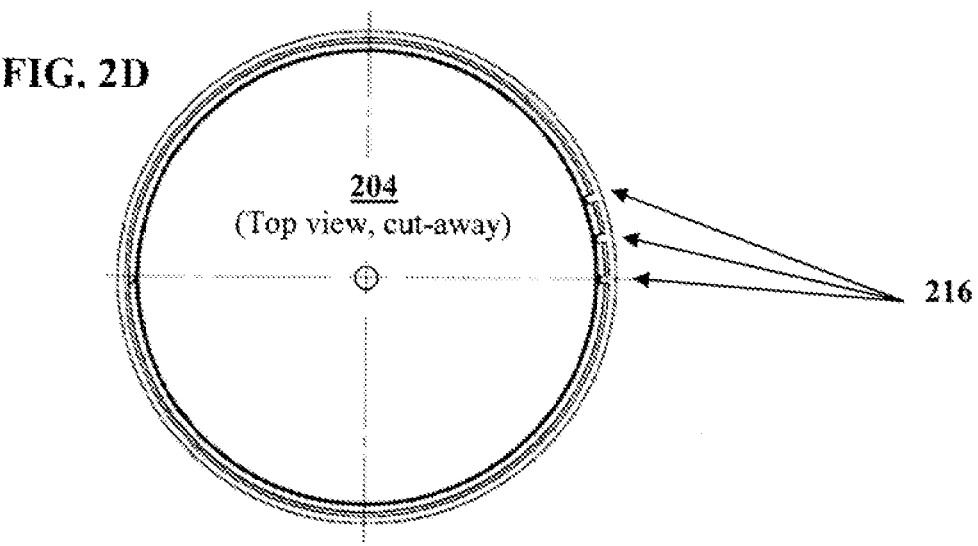

FIG. 4A
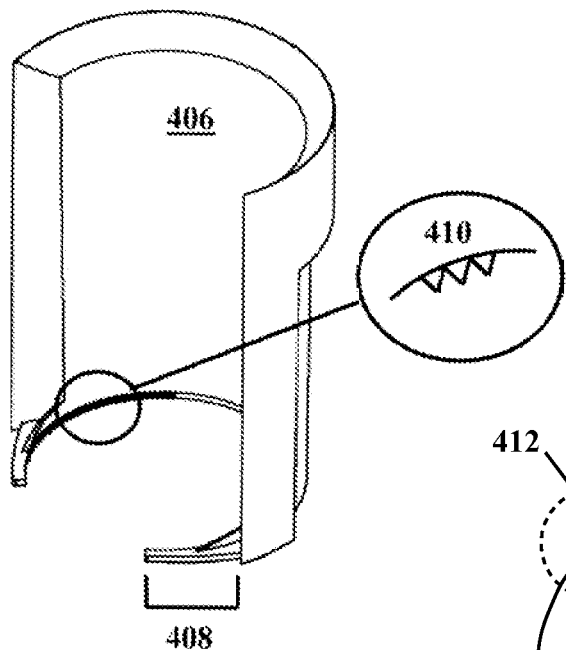
FIG. 4B
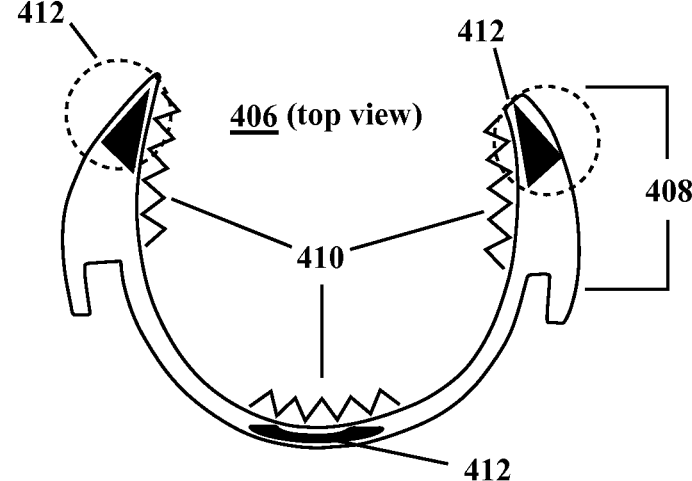
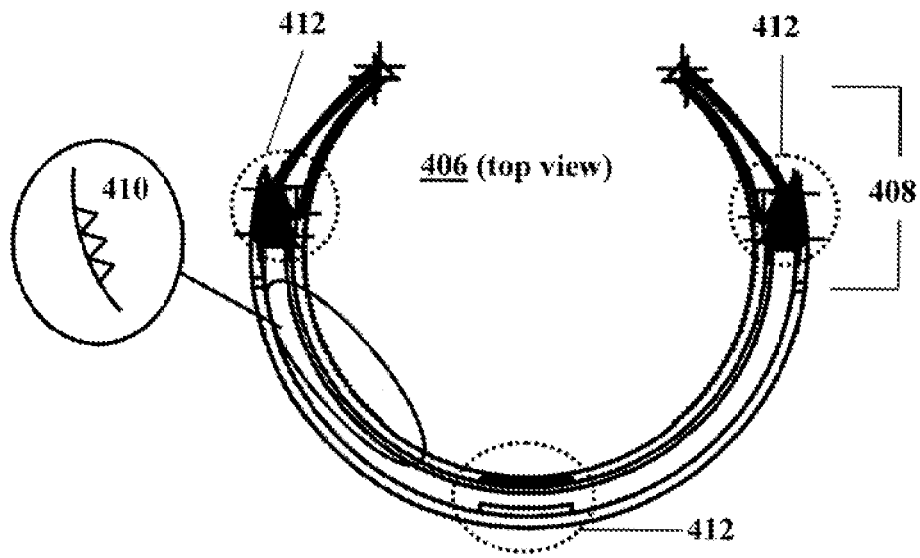
FIG. 4C

POSITION INDICATOR ON LIQUID SAMPLE CONTAINER

CROSS-REFERENCE TO RELATED APPLICATIONS

This application claims priority to U.S. Provisional Application Ser. No. 61/525,062, entitled "CUP AND LID WITH INSERT," filed Aug. 18, 2011, which is incorporated by reference.

BACKGROUND

An area of ongoing research and development is in improving containers for biological samples. A problem is that mistakes can be made when using or handling such containers. Any advancement that resulted in improvements in the ability to properly use or handle biological sample containers would be desirable to reduce the probability of mistakes, accidents, or erroneous test results on the biological samples in the containers. These examples of ways to improve use of biological sample containers are intended to be illustrative and not exclusive or exhaustive.

BRIEF DESCRIPTION OF THE DRAWINGS

FIGS. 2A-2D depict a diagram of alternative views of an example of a liquid sample container assembly with an audible position indicator.

FIGS. 4A-4D depict diagrams of alternative views of an example of an insert that can be used in combination with a quid sample container assembly.

DETAILED DESCRIPTION

Figure 1A:
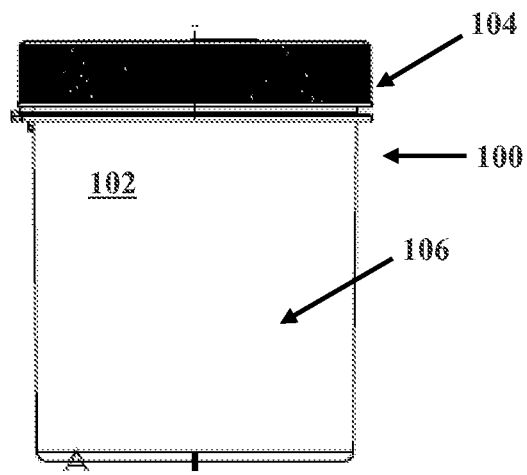
FIGS. 1A-1D depict a diagram of alternative views of an example of a liquid sample container assembly with a visual position indicator.

FIGS. 1A-1D depict a diagram 100 of alternative views of an example of a liquid sample container assembly with a visual position indicator. In the example of FIGS. 1A-1D, the assembly includes a cup or container 102 (hereinafter "the cup 102") for holding liquids, such as liquid biological samples, a lid 104, and an insert 106. In the example in FIGS. 1A-1D, the cup 102 has threads 108 and a visual closed or sealed position indicator 110 ("the visual sealed position indicator 110"), and the lid 104 has a visual closed or sealed position indicator 112 ("the visual sealed position indicator 112").

The visual sealed position indicators 110, 112 are visually distinct areas on the cup 102 and the lid 104 that align when the lid 104 is tightened to an optimal generally predetermined range. The optimal range is indicative of a recommended closed position. Depending upon the implementation, seals formed when the position indicators 110, 112 do not indicate a properly closed position can be acceptable in certain conditions or in accordance with certain standards because the optimal range is intended to represent a conservative estimate of a proper seal; it is safe to err on the side of a smaller range than is adequate.

Figure 1B:
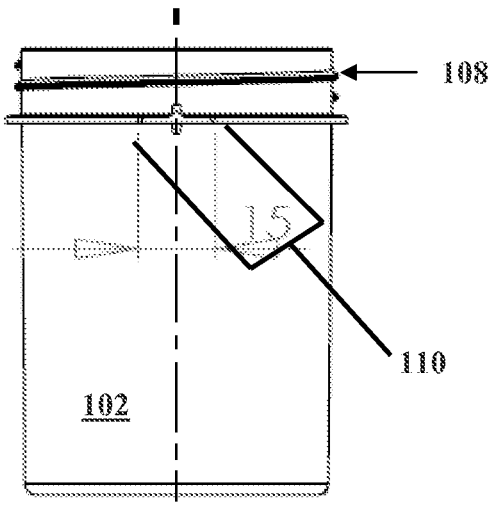

In the example of FIG. 1B, the visual sealed position indicator 110 is depicted as a horizontal protrusion below the threads 108 of the cup 102. In this specific example, the horizontal protrusion is sufficiently large, and protrudes sufficiently far from the surface of the cup 102, to be visible both from the side of the cup 102, and from the top of the cup 102 even when the lid 104 is in place. The visual sealed position indicator 110 is depicted as having a particular size for illustrative purposes only; the visual sealed position indicator 110 can be smaller or larger than is represented in the example of FIG. 1B. In general, a visual sealed position indicator on the cup can be implemented as a convenient visually distinct area of the cup, positioned below a portion of the cup that is covered by the lid when the lid is secured (which is likely to be below the threads of the cup) and that is less than the circumference of the cup. When measuring vertical position, as opposed to circumferential position relative to the cup as is described in this paper as the primary example, the visual sealed position indicator can extend partially under the portion of the cup covered by the lid, but at least some will remain visible, or the visual sealed position indicator can extend over the outer circumference of the lid.

In a specific implementation, the visual sealed position indicator 110 is a visibly differently textured portion of the cup 102 that is less than the circumference of the cup 102. In another specific implementation, the visual sealed position indicator is a portion of the cup with a different opacity from the rest of the cup. In other specific implementations, the visual sealed position indicator is a portion of the cup with a different visual etched or raised design. In other implementations, the visual sealed position indicator on the cup is indicated by lines, words or symbols.

In operation, the visual closed or sealed position indicators 110, 112 inform a user when the lid 104 is sufficiently closed so that the contents of the cup 102 will not leak. The lid 104 can be sufficiently tight to prevent leaking through a range of orientations as it is screwed down. In the example of FIGS. 1A-1D, this range begins when the visual sealed position indicators 110, 112 begin to overlap or align. As the lid is tightened, the visual sealed position indicators 110 and 112 overlap more or come more into alignment, indicating the lid 104 is even secure.

Figure 1C:
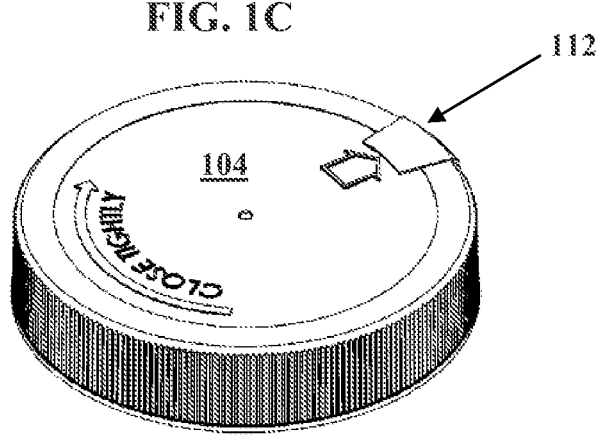
Figure 1D:
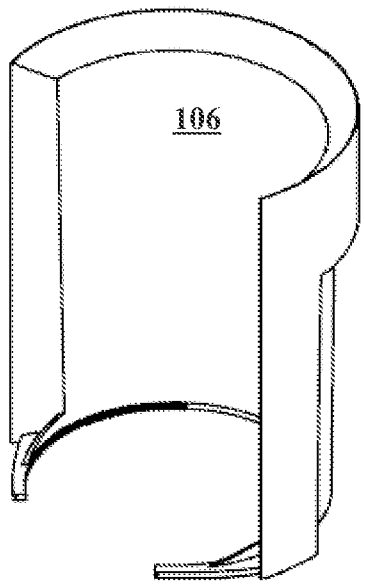

The visual sealed position indicator 112 is a portion of the lid 104 that is visually distinct from the outside surface of the lid 104, and less than the circumference of the lid 104. This visual sealed position indicator aligns with the visual sealed position indicator 110 when the lid 104 is tightened on the cup 102 to within the optimal range. In the example in FIG. 1C, the visual sealed position indicator on the lid 112 is a slightly raised flat area on the top of the lid 104 near the edge and continuing down the outside wall of the lid 104. Advantageously, in this specific example, the visual sealed position indicator 112 can be seen from both the top and side of the lid 104. The visual sealed position indicator 112 is depicted as having a particular size for illustrative purposes only; the visual sealed position indicator 112 can be smaller or larger than is represented in the example of FIG. 1C. In general, a visual sealed position indicator on the lid can be implemented as a convenient visually distinct area of the lid, positioned on the outer circumference of the lid and that is less than the circumference of the cup.

In a specific implementation, the visual sealed position indicator 112 is a visibly differently textured portion of the lid 104 that is less than the circumference of the lid 104. In another specific implementation, the visual sealed position indicator is a portion of the lid with a different opacity from the rest of the lid. In other specific implementations, the visual sealed position indicator is a portion of the lid with a different visual etched or raised design. In other implementations, the visual sealed position indicator on the lid is indicated by lines, words or symbols.

FIGS. 2A-2D depict a diagram of alternative views of an example of a liquid sample container assembly with an audible position indicator. In the example of FIGS. 2A-2D the cup 202 has threads 208 and has an audible closed or sealed position indicator 212 ("the audible sealed position indicator 212"), and the lid 204 has threads 214 and has audible closed or sealed position indicators 216 ("the audible sealed position indicators 216").

In the example in FIGS. 2A and 2B, the audible closed or sealed position indicator 212 on the cup 202 is a single protrusion extending outward from the surface of the cup 202 immediately below the threads 208. In the example in FIGS. 2C and 2D, the audible closed or sealed position indicators 216 on the lid 204 are three protrusions along the rim of the lid 204 immediately below the threads 214, that protrude in toward the center of the lid 204.

In operation, the audible closed or sealed position indicators 212, 216 inform a user when the lid 204 is sufficiently closed so that the contents of the cup 202 will not leak. In the example of FIGS. 2A-2D, when the lid 204 is tightened on the cup, the audible tightness or sealed position indicators 216 on the lid 204 contact the audible sealed position indicator 212 on the cup 202 in succession and make a series of noises or "clicks" as the lid is tightened. In the specific example of FIGS. 2A-2D, the last noise or "click" in the series indicates to the user that the lid has been tightened to an optimal generally predetermined position. The optimal position is indicative of a recommended closed position. In general, this is a conservative estimate of the tightness position needed to prevent the contents of the cup from leaking.

In the specific implementation in FIGS. 2A-2D, the protrusions that form the audible sealed position indicators 216 on the lid 204 and the audible sealed position indicator 212 on the cup 202, are rectangular in shape. In another implementation, the audible sealed position indicators on the lid 204 and the audible sealed position indicator on the cup 202 are triangular in shape. The audible sealed position indicators 216 on the lid 204 and the audible sealed position indicator 212 on the cup 202 can be other shapes as well. Many shapes permit the corresponding lid and cup audible sealed position indicators 212, 216 to contact each other in such a manner as to make a noise or series of noises.

The lid 204 can be sufficiently tight to prevent leaking through a range of orientations as it is screwed down. In another specific implementation of the lid 204 and cup 202 with audible sealed position indicators 212, 216, this range begins when the first audible sealed position indicator 216 on the lid 204 contacts the audible sealed position indicator 212 on the cup 202, making the first "click." As each successive audible sealed position indicator 216 on the lid 204 contacts the audible sealed position indicator 212 on the cup 202, this indicates to the user that the lid 204 is even more secure.

In another specific implementation of the lid 204 and cup 202 with audible sealed position indicators, there is a single audible sealed position indicator on the lid 204 and a single audible sealed position indicator on the cup 202. In operation, this single sealed position indicator on the lid 204 contacts the single sealed position indicator on the cup 202 and makes an audible noise or "click" that indicates to the user that the lid has been tightened to an optimal generally predetermined position that is indicative of a recommended closed position.

In another specific implementation of the lid 204 and cup 202 with audible sealed position indicators, there is a single audible sealed position indicator on the lid 204 and more than one audible sealed position indicators on the cup 202. In operation, the single audible sealed position indicator on the lid 204 contacts the multiple audible sealed position indicators on the cup 202 in succession making a series of noises or "clicks" as the lid 204 is tightened. This configuration can be implemented so that in operation, the last noise or "click" in the series indicates to the user that the lid 204 has been tightened to a recommended closed position. This configuration can also be implemented so that in operation, the first "click" indicates to the user that the lid 204 has been tightened to a recommended closed position, and each successive click indicates to the user that the lid 204 is even more secure of may be approaching non-optimal over-tightening.

In another specific implementation of the lid 204 and cup 202 with audible sealed position indicators, the cup and lid audible sealed position indicators are textured areas on the cup 202 and lid 204. Such textured areas can be located above, below, or within the threads on the cup and lid 208, 214. The textured areas are positioned partially around the inside-facing circumference of the lid 204 and partially around outside-facing circumference of the cup 202 so that they rub against each other as the lid 204 is being tightened. In operation, this makes a noise as the lid 204 is tightened on the cup 202. The textured areas are positioned so that, as the lid 204 becomes tight enough to prevent the contents of the cup 202 from leaking, the textured areas move all the way past each other, stop rubbing, and stop making the noise. The cessation of the noise informs the user that the lid 204 is sufficiently tight that the contents of the cup 202 will not spill.

Figure 3A:
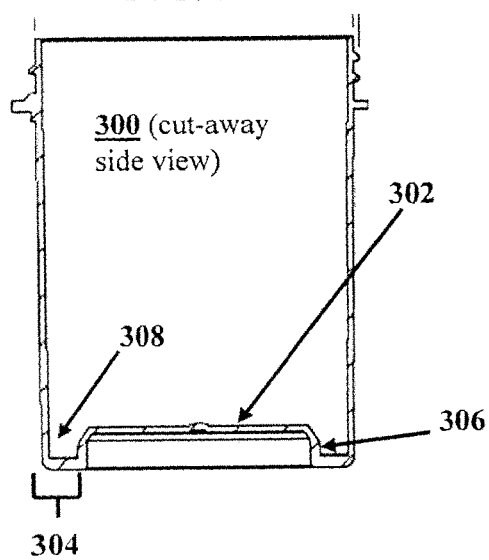
FIGS. 3A-3C depict a diagram of alternative views of an example of a liquid sample container assembly having a cup with a raised center portion of the bottom.
Figure 3B:
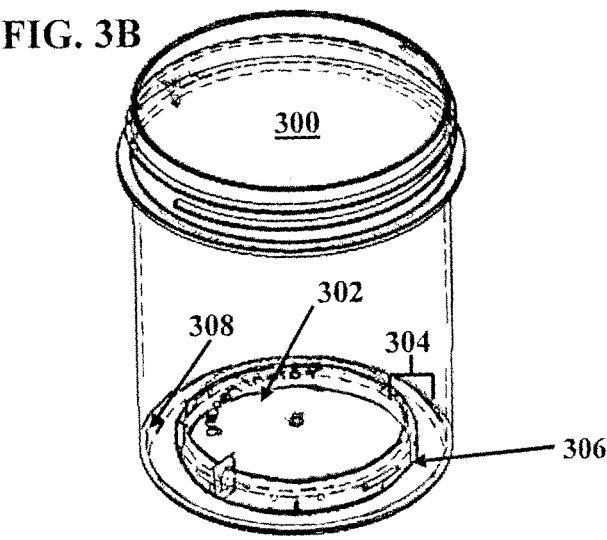
Figure 3C:
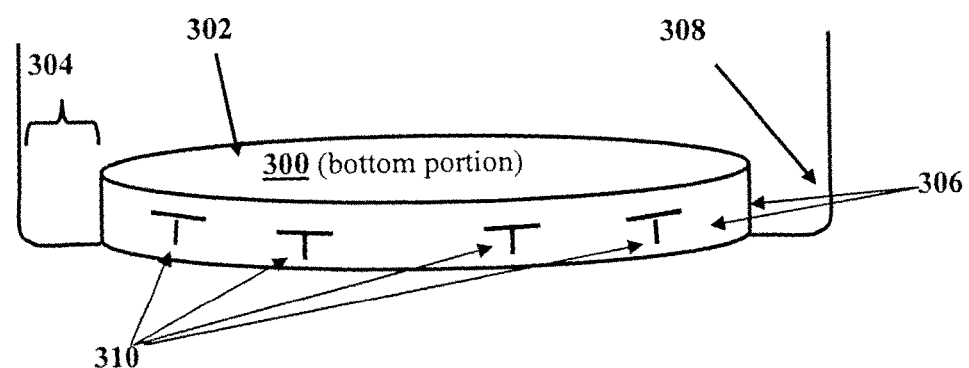
Figure 4D:
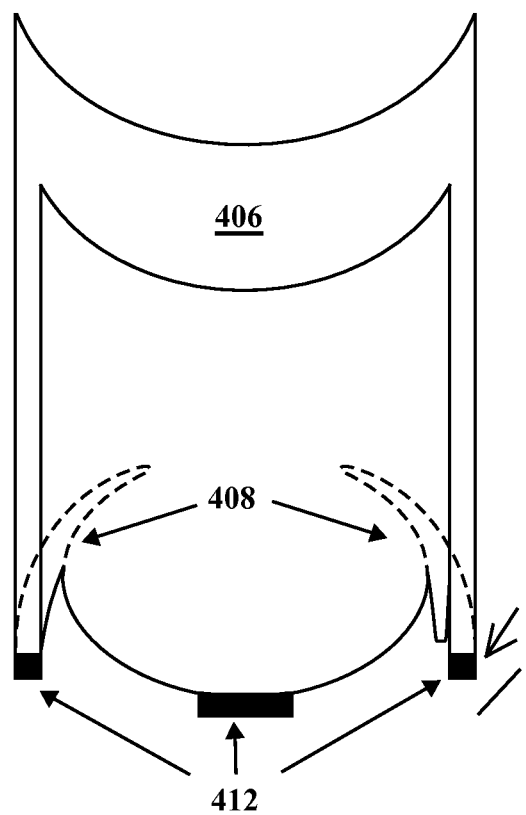

FIGS. 3A-3C depict a diagram of alternative views of an example of an apparatus having a cup 300 with a raised center portion of the bottom 302 ("the raised central bottom 302"). In the example of FIGS. 3A-3C raised central bottom 302 creates a channel, or trough, 304 ("the channel 304") around the circumference of the bottom of the cup 300. In operation, the raised bottom 302 and channel 304 have the advantage that they ensure that small volumes of liquid samples placed in the cup collect, or are concentrated, in the channel around the perimeter of the cup. This collection or concentration of small volume samples in the channel ensures that there is sufficient liquid in the channel to wet the bottoms of testing strips placed in the cup 300. (insertion of test strips into the cup is discussed further below.)

In another specific implementation, the raised bottom area is completely raised over half of the bottom of the cup 300, so that it "fills in" the channel in half of the cup. In this configuration, the channel does not form a complete circle, but only forms half of a circle. In this configuration, the insert 406, an example of which is shown in FIGS. 4A-4D, and discussed further below, does not have "wings" or brackets. In another specific implementation, the channel is more than half of a complete circle. In another specific implementation, the channel is less than half of a complete circle.

In the example in FIGS. 3A-3C, the raised central bottom 302 and channel 304 have a wall of the raised central bottom facing into the channel 306 ("the inner channel sidewall 306") and an interior wall of the cup facing into the channel 308 ("outer channel sidewall 308"). The sidewalls can be modified with protrusions into the channel 310 ("the channel protrusions 310") that project into the channel and interact with the insert 406, an example of which is depicted in FIGS. 4A-4D, and discussed further below. In the example in FIGS. 3A-3C, the inner sidewall 306 is enhanced with horizontal and vertical channel protrusions 310 in the form of ribs or ridges projecting into the channel. The horizontal and vertical channel protrusions 310 are arranged in "T" formations.

In another specific implementation, the horizontal and vertical channel protrusions are arranged in an "L" formation. In another specific implementation, the horizontal and vertical channel protrusions are arranged in a "+" formation. In another specific implementation, the horizontal and vertical channel protrusions are arranged as separate "|" and "-" shapes that do not contact each other. The horizontal and vertical channel protrusions 310 can be spaced around, or distributed along the inner sidewall surface in many different patterns.

In another specific implementation, the horizontal and vertical channel protrusions on the inner channel sidewall 306 are not ribs or ridges, but instead are protrusions in the shape of "bumps" or convex dimples. In another specific implementation, discussed further below, the protrusions are replaced with indentations or concave dimples in the inner channel sidewall 306.

In another specific implementation, rather than being placed on the inner channel sidewall 306, the horizontal, vertical or bump-like channel protrusions are located on the outer channel sidewall 308 and project into the channel. In another specific implementation, discussed further below, there are indentations or concave dimples in the outer channel sidewall 308.

FIGS. 4A-4D depict diagrams of alternative views of an example of an insert 406 that can be used in combination with the cup 300, and lid (not shown) and that has stabilization "wings" or braces around its bottom edge 408 and insert protrusions 410 for interlocking with or gripping the raised central bottom 302 of the cup 300. In the example of FIGS. 4A-4D the insert 406 is in the general shape of a tube cut length-wise. The insert has a smaller diameter than the cup 300 and can slide inside the cup. In the example in FIGS. 4A-4D, the diameter of the insert is smaller than the cup 300 but slightly larger than the raised central bottom 302. In operation, when the example insert 406 depicted in FIGS. 4A-4D is placed into the cup 300, the bottom edge of the insert 406 slides into the channel 304. When the bottom of the insert 406 is in the channel 304, the inside, bottom surface of the insert contacts the inner channel sidewall 306.

In the example in FIGS. 4A-4D, the insert 406 has projecting "feet" or raised areas 412 that project downward from the insert's bottom surface. When the insert 406 is placed into the cup 300 these areas or "feet" 412 elevate the insert 406 a slightly from the bottom of the channel 304. Among other things, this arrangement has the advantage that in operation, the feet 412 ensure that biological samples in the cup 300 and in the channel 304 can flow underneath the bottom edge of the insert 406 and wet the test strips held in the insert 406.

In the example in FIGS. 4A-4D, the insert 406 has two "wings" or braces 408 along its bottom edge that project further around the circle formed by the radius of the insert 406. Because the "wings" or braces 408 are located at the bottom, in the example in FIGS. 4A-4D, the bottom edge of the insert 406 makes a more complete circle than the top edge. In the example in FIGS. 4A-4D, these wings or braces 408 make a stable base and prevent the insert 406 from tipping toward the center of the cup 300 when it is inserted into the cup. Among other things, in operation this has the advantage of ensuring that the bottoms of all of the test strips held in the insert 406, contact the sample in the cup 300 and are wet by the sample. Moreover, in operation, the example shown in FIGS. 4A-4D has the advantage that it helps hold the insert 406, and the test strips held in the insert 406, in a position in which they can be concealed behind a removable label affixed to the outside of the cup 300 until it is appropriate that any results displayed by the test strips are observed. For example, the person providing the sample that is to be tested should not be able to observe the test strips and any results that may be displayed on the test strips. Therefore, the insert 406 should remain upright and secure while the sample is gathered. In addition, people who handle the cup 300, lid (not shown) and insert 406 may not be permitted to view results displayed on the test strips for privacy or security reasons. This also makes it desirable that the insert 406 and test strips remain securely upright so that they can be concealed by a removable label on the outside of the cup 300. Finally, when the appropriate person is ready to view the results displayed on the test strips it is advantageous if the insert is upright and secure so that the test strips are held in an orderly position in proximity to the wall of the in the cup 300 and can be easily viewed when the label on the outside of the cup is removed.

In the example in FIGS. 4A-4D, the insert 406 also has small insert protrusions or "teeth" 410 projecting inward, around the insert's inner surface, along its bottom edge. In the example in FIGS. 4A-4D, the insert protrusions 410 are triangular-shaped "teeth." In operation, when the insert 406 is placed inside the cup 300 and the bottom of the insert 406 slides into the channel 304, the inside bottom edge of the insert contacts the inner channel sidewall 306. In this configuration, the insert protrusions 410, or "teeth," contact the horizontal and vertical ribs 310 located on the inner channel sidewall 306. The insert protrusions 410, or "teeth," and the horizontal and vertical ribs 310 tend to interlock, preventing the insert from moving inside the cup 300. In this configuration, the horizontal ribs 310 interacting with the teeth 410, prevent the insert from moving up and down, while the vertical ribs 310 interacting with the teeth 410 prevent the insert from slipping side to side. In addition, in this configuration, in operation the wings 408 slip under the horizontal ribs 310. The horizontal ribs 310 tend to "lock" the wings 408 of the insert down in the cup and prevent the insert from sliding up and down. As described previously, fixing the upright and horizontal position of the insert 406 has the advantage of holding the insert 406 and test strips upright and secure, so that, among other things, they can be concealed behind a removable label and easily viewed only by the appropriate person.

In another specific implementation, the insert protrusions are square-shaped "teeth." In another specific implementation, the insert protrusions are rounded or bump-like. In this implementation, the horizontal and vertical ribs 310 can be the same as depicted in the example shown in FIGS. 3A-3C, and can interlock with the bump-like insert protrusions. However, in the implementation in which the insert protrusions are rounded or bump-like, the horizontal and vertical ribs 310 can be replaced by indentations or concave dimples on the inner channel sidewall 306. In this latter configuration, in operation, when the bottom of the insert 406 is placed in the channel 304, the bump-like insert protrusions fit into the indentations or concave dimples on the inner channel sidewall 306, "locking" the insert in place.

In another specific implementation, the triangular or square, teeth-like insert protrusions project outward, around the insert's outer surface, along its bottom edge. In another specific implementation, the insert protrusions are rounded or bump-like, and project outward, around the insert's outer surface, along its bottom edge. In these two specific implementations, the horizontal and vertical ribs are located on the outer sidewall surface 308 and project into the channel 304. In operation of these two implementations, the outward facing insert protrusion teeth or bumps interlock with the inward facing horizontal and vertical ribs on the outer sidewall surface 308 when the bottom of the insert is placed in the channel 304.

In another specific implementation, the insert protrusions are rounded or bump-like and project outward, around the insert's outer surface, along its bottom edge. In this specific implementation, the horizontal and vertical ribs on the outer sidewall surface 308 can be replaced by indentations or concave dimples on the outer sidewall surface 308. In this configuration, in operation when the bottom of the insert is placed into the channel, the outward-facing, bump-like insert protrusions fit into the indentations or concave dimples on outer sidewall surface 308, "locking" the insert in place.

Figure 5:
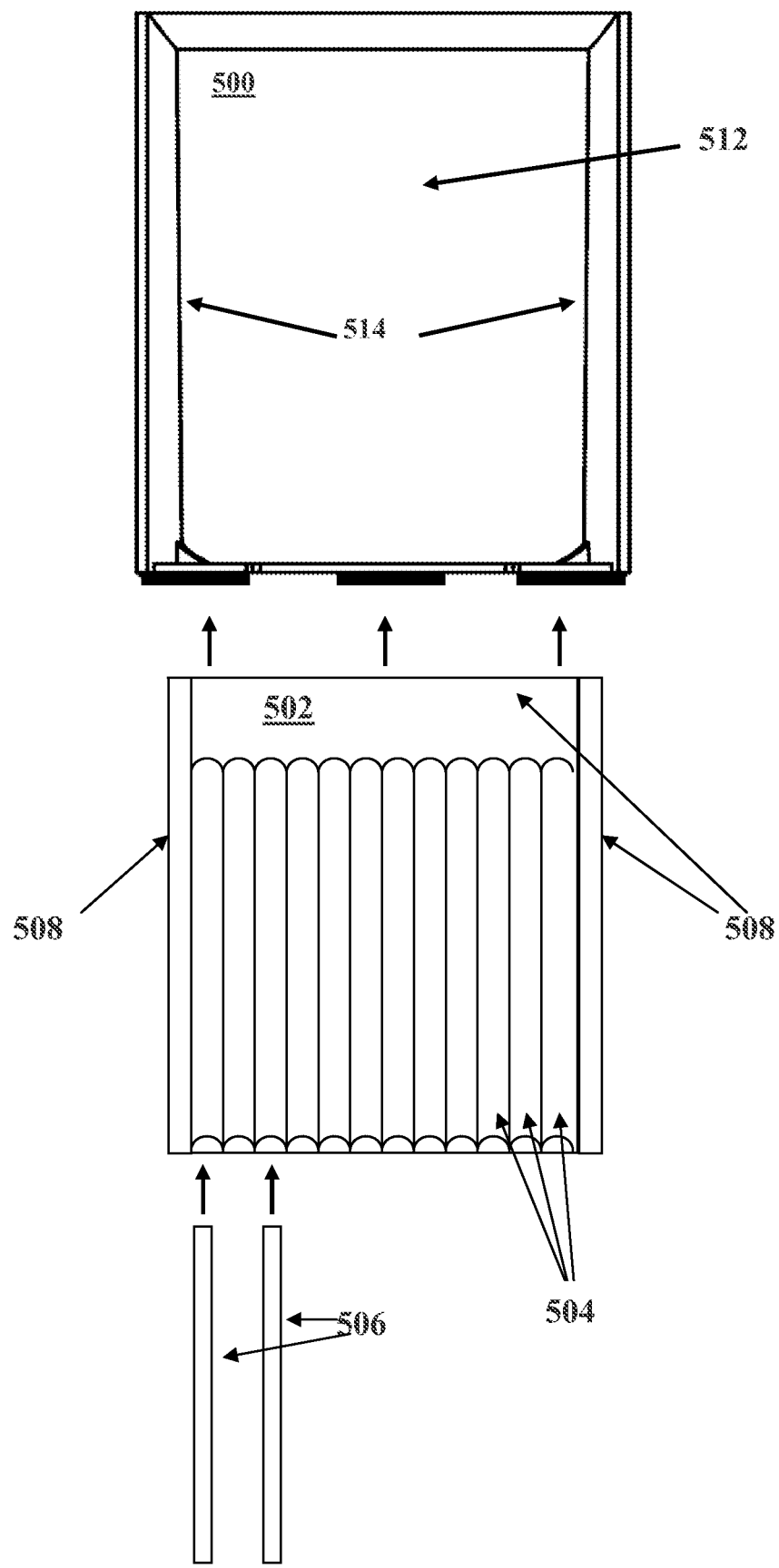
FIG. 5 depicts a diagram an example of test strips and a test strip sleeve that can be used in combination with the insert depicted in FIGS. 4A-4D.

FIG. 5 depicts a diagram an example of test strips and a test strip sleeve that can be used in combination with the insert 106, 406 and 500. In the example in FIG. 5 the insert 500 has a test-strip holding window 514, or bracket, with a groove 512 surrounding it. The test-strip holding window 514, or bracket, and groove 512, can hold a sleeve containing test strips 506. In operation, test strips are held vertically in the insert 500, so that the ends of the test strips may be wet by the biological sample in the cup, permitting the test strips to be used to detect the presence of various chemicals, such as illegal drugs.

In the specific implementation shown in FIG. 5, the test strip sleeve is a clear plastic device 502, with multiple tubes or channels 504 into which test strips 506 can be inserted. In this configuration, in operation the edge 508 of the sleeve fits into the groove 514 around the test-strip holding window 512, or bracket. The test strips can be used to test the liquid sample in the cup for various substances, such as illegal drugs. The test strips usually, but do not necessarily have to, display a test result on their surface after they have contacted the liquid sample in the cup. In the example configuration shown in FIG. 5 the test-strip holding bracket 512 holds the test strip sleeve 502, and test strips 506 therein, vertically. In operation, when a liquid or sample, such as urine is present in the cup, it collects in the channel 304. In operation, when the insert 500 carrying test strip sleeve 502 and test strips 506 is placed into the cup 300, the bottom of the insert 500, and the bottoms of test strips 506 it carries, slide down into the channel 304. In this configuration, when the volume of the sample in the cup is small, the Channel 304 directs the sample to the bottoms of the test strips 506 and ensures that the test-strips are wet.

In a specific implementation, the visual 110, 112 and audible 212, 214 sealed position indicators can be used in combination. In other specific implementations, the cup 300 and insert 406 may be used in combination with either or both of the visual 110, 112 and audible 212, 214 sealed position indicators.

In an alternative implementation, the lid 104 or 204 can be pressed onto the cup 102 or 202 rather than being screwed onto the cup. The visual sealed position indicators and/or audible sealed position indicators can be configured to indicate a recommended sealed position when the lid is pressed sufficiently far onto the cup.

The invention claimed is:

1. An assembly comprising:
a cup having a first visual sealing indicator and a single first audible sealing indicator; and
a lid having a second visual sealing indicator and a plurality of second audible sealing indicators, the second visual sealing indicator including a slightly raised flat area on a top of the lid and down an outside wall of the lid that allows the second visual sealing indicator to be viewed from the top of the lid and a side of the lid, the first visual sealing indicator including a horizontal protrusion that allows the first visual sealing indicator to be viewed from a side of the cup and a top of the cup when the lid is in place;
wherein, in operation, the lid is screwed on the cup to a sealing indicator position where the first visual sealing indicator and the second visual sealing indicator are aligned and a series of successive audible sounds are generated as the lid is screwed onto the cup via contact of the single first audible sealing indicator of the cup and the plurality of second audible sealing indicators of the lid, the audible sounds indicating formation of a liquid tight seal being formed between the lid and cup,
wherein the single first audible sealing indicator includes a first protrusion that extends out from an outer sidewall of the cup and the plurality of second audible sealing indicators includes a second protrusion that extends out from an inner sidewall of the lid, the first protrusion and the second protrusion shaped to produce the audible sound when the first protrusion and the second protrusion come into contact with each other, and
wherein the plurality of second audible sealing indicators are disposed proximate one another and partially around the circumference of the lid.

2. An assembly comprising:
a container having a first visual sealing indicator means and a single first audible sealing indicator; and
a cap having a second visual sealing indicator means and a plurality of second audible sealing indicators, the second visual sealing indicator means including a slightly raised flat area on a top of the cap and down an outside wall of the cap that allows the second visual sealing indicator to be viewed from the top of the cap and a side of the cap, the first visual sealing indicator means including a horizontal protrusion that allows the first visual sealing indicator means to be viewed from a side of the cup and a top of the cup when the cap is in place;
wherein, in operation, the cap is pressed on the container to a sealing indicator position where the first visual sealing indicator means is visibly matched with the second visual sealing indicator means and a series of successive audible sounds are generated as the lid is screwed onto the cup via contact of the single first audible sealing indicator of the cup and the plurality of second audible sealing indicators of the lid, the audible sounds indicating formation of a liquid tight seal being formed between the lid and cup,
wherein the single first audible sealing indicator includes a first protrusion that extends out from an outer sidewall of the cup and the plurality of second audible sealing indicators includes a second protrusion that extends out from an inner sidewall of the lid, the first protrusion and the second protrusion shaped to produce the audible sound when the first protrusion and the second protrusion come into contact with each other, and wherein the plurality of second audible sealing indicators are disposed proximate one another and partially around the circumference of the lid.

3. The assembly of claim 1, wherein the cup includes threads for securing the lid to the cup, further wherein the first visual sealing indicator is a horizontal protrusion positioned beneath the threads.

4. The assembly of claim 3, wherein the horizontal protrusion extends out from the cup a distance such that it can be seen from the top of the lid when the lid is coupled to the cup.

5. The assembly of claim 1, wherein the first visual sealing indicator includes an etched or raised portion to visually differentiate the first visual sealing indicator from the cup.

6. The assembly of claim 1, wherein the second visual sealing indicator is visually distinct from the lid.

7. The assembly of claim 1, wherein the second visual sealing indicator is raised above the top of the lid.

8. The assembly of claim 1, wherein the second visual sealing indicator extends out from an outside wall of the lid.

9. The assembly of claim 1, wherein the lid has a first opacity and the second visual sealing indicator has a second opacity, the second opacity being different from the first opacity.

10. The assembly of claim 1, wherein the second visual sealing indicator includes an etched or raised portion to visually differentiate the second visual sealing indicator from the lid.

11. The assembly of claim 1, wherein the first protrusion and the second protrusion are either rectangular or triangular in shape.

12. The assembly of claim 2, wherein the first protrusion and the second protrusion are either rectangular or triangular in shape.

* * * * *